United States Patent
Moran, Jr.

(10) Patent No.: US 8,617,085 B2
(45) Date of Patent: Dec. 31, 2013

(54) BONE TISSUE EXTRACTING DEVICE AND METHOD

(76) Inventor: Antonio Moran, Jr., Brunswick, GA (US)

( * ) Notice: Subject to any disclaimer, the term of this patent is extended or adjusted under 35 U.S.C. 154(b) by 295 days.

(21) Appl. No.: 12/747,899

(22) PCT Filed: Aug. 14, 2009

(86) PCT No.: PCT/IB2009/008072
§ 371 (c)(1),
(2), (4) Date: May 5, 2011

(87) PCT Pub. No.: WO2010/076663
PCT Pub. Date: Jul. 8, 2010

(65) Prior Publication Data
US 2011/0184312 A1  Jul. 28, 2011

(51) Int. Cl.
*A61B 10/02* (2006.01)
*A61B 17/3205* (2006.01)

(52) U.S. Cl.
CPC ......... *A61B 10/025* (2013.01); *A61B 17/32053* (2013.01)
USPC .............................. 600/564; 600/566; 606/80

(58) Field of Classification Search
USPC ............... 600/566, 565, 562, 564; 606/80, 81
See application file for complete search history.

(56) References Cited

U.S. PATENT DOCUMENTS

| | | | | |
|---|---|---|---|---|
| 2,594,621 A * | 4/1952 | Derrick | ......................... | 600/577 |
| 4,686,997 A * | 8/1987 | Oloff et al. | ..................... | 600/436 |
| 4,815,462 A * | 3/1989 | Clark | ............................. | 606/170 |
| 5,207,697 A * | 5/1993 | Carusillo et al. | .............. | 606/167 |
| 5,971,983 A * | 10/1999 | Lesh | ................................ | 606/41 |
| 6,033,369 A * | 3/2000 | Goldenberg | ................... | 600/567 |
| 6,110,176 A * | 8/2000 | Shapira | ............................ | 606/80 |
| 6,113,555 A * | 9/2000 | Parmigiani | .................... | 600/579 |
| 6,251,121 B1 * | 6/2001 | Saadat | ........................... | 606/180 |
| 6,358,252 B1 * | 3/2002 | Shapira | ........................... | 606/80 |
| 6,461,302 B1 * | 10/2002 | Thompson | ..................... | 600/439 |
| 6,540,694 B1 * | 4/2003 | Van Bladel et al. | ........... | 600/564 |
| 6,796,957 B2 * | 9/2004 | Carpenter et al. | ......... | 604/93.01 |
| 6,846,314 B2 * | 1/2005 | Shapira | ........................... | 606/80 |
| 6,960,198 B2 * | 11/2005 | Sarmiento | ..................... | 604/411 |
| 7,081,123 B2 * | 7/2006 | Merboth et al. | .............. | 606/185 |
| 7,226,432 B2 * | 6/2007 | Brown | .......................... | 604/122 |
| 7,278,972 B2 * | 10/2007 | Lamoureux et al. | .......... | 600/567 |
| 7,396,343 B2 * | 7/2008 | Brown | .......................... | 604/122 |
| 7,481,817 B2 * | 1/2009 | Sauer | ............................. | 606/170 |
| 7,611,473 B2 * | 11/2009 | Boock et al. | .................. | 600/564 |
| 7,699,850 B2 * | 4/2010 | Miller | ............................ | 606/80 |
| 7,998,086 B2 * | 8/2011 | Boock et al. | ................. | 600/566 |
| 2003/0069543 A1 * | 4/2003 | Carpenter et al. | ............ | 604/190 |
| 2003/0105414 A1 * | 6/2003 | Leong | ............................ | 600/576 |
| 2003/0225344 A1 * | 12/2003 | Miller | ............................ | 600/568 |
| 2003/0225411 A1 * | 12/2003 | Miller | ............................ | 606/80 |

(Continued)

*Primary Examiner* — Sean Dougherty
*Assistant Examiner* — Michael C Stout
(74) *Attorney, Agent, or Firm* — Jonathan R. Smith; Jonathan Rigdon Smith, PC (57) ABSTRACT

A bone tissue extracting device operable with one hand comprises an ergonomic handle containing a forward and reverse cannula driver and a vacuum source. The device uses a disposable sterile single use cannula/trocar and disposable vacuum containers. The device and method for use improve the ability of a physician to locate accurately the target tissue in a patient, increase the probability that one or more suitable samples will be recovered from the patient at a single attempt, decrease attendant tissue trauma and patient discomfort, and decrease the chance of infection.

18 Claims, 8 Drawing Sheets

(56) References Cited

U.S. PATENT DOCUMENTS

| | | |
|---|---|---|
| 2003/0229315 A1* | 12/2003 | Leong et al. .................. 604/263 |
| 2004/0215102 A1* | 10/2004 | Ikehara et al. ................ 600/562 |
| 2005/0059905 A1* | 3/2005 | Boock et al. .................. 600/567 |
| 2005/0165404 A1* | 7/2005 | Miller ............................. 606/80 |
| 2005/0171504 A1* | 8/2005 | Miller ........................... 604/506 |
| 2005/0261693 A1* | 11/2005 | Miller et al. .................... 606/80 |
| 2005/0288605 A1* | 12/2005 | Pellegrino et al. ............ 600/562 |
| 2006/0030785 A1* | 2/2006 | Field et al. .................... 600/567 |
| 2006/0036212 A1* | 2/2006 | Miller ............................. 604/48 |
| 2006/0052790 A1* | 3/2006 | Miller ............................. 606/80 |
| 2006/0058737 A1* | 3/2006 | Herweck et al. ......... 604/164.01 |
| 2006/0129063 A1* | 6/2006 | Thompson et al. ........... 600/566 |
| 2006/0167379 A1* | 7/2006 | Miller ........................... 600/566 |
| 2006/0247552 A1* | 11/2006 | Ikehara et al. ................ 600/562 |
| 2007/0049945 A1* | 3/2007 | Miller ............................. 606/86 |
| 2007/0066987 A1* | 3/2007 | Scanlan et al. ............... 606/184 |
| 2007/0156064 A1* | 7/2007 | Ritchart et al. ............... 600/564 |
| 2007/0270775 A1* | 11/2007 | Miller et al. .................. 604/506 |
| 2007/0282345 A1* | 12/2007 | Yedlicka et al. ................ 606/80 |
| 2008/0015468 A1* | 1/2008 | Miller ........................... 600/568 |
| 2008/0045965 A1* | 2/2008 | Miller et al. .................... 606/80 |
| 2008/0140014 A1* | 6/2008 | Miller et al. .................. 604/180 |
| 2008/0215056 A1* | 9/2008 | Miller et al. .................... 606/80 |
| 2008/0221580 A1* | 9/2008 | Miller et al. .................... 606/80 |
| 2010/0222664 A1* | 9/2010 | Lemon et al. ................. 600/409 |
| 2011/0245715 A1* | 10/2011 | Quick et al. .................. 600/566 |

* cited by examiner

BONE TISSUE EXTRACTING DEVICE AND METHOD

FIELD OF INVENTION

This invention is in the field of surgery and surgical instruments, more specifically in the field of instruments for obtaining tissue samples, and more specifically, automated instruments.

BACKGROUND OF INVENTION

In specific instances it is necessary for a physician to obtain a sample of bone marrow. Most commonly, the sample is biopsied to determine the presence of disease, although other purposes may exist, e.g., recovery of cells for transplantation. A biopsy may be prescribed to remove liquid aspirates from the marrow space as well as a core sample of the bone marrow to determine whether cancer or other disease is present. Liquid aspirate must be drawn from the marrow cavity for cytological study and a core sample of marrow material must be obtained if histological study is desired.

In the conventional prior art procedure, the physician penetrates the hard bone of the patient with a cannula/trocar combined needle from a bone marrow biopsy set (see, e.g., U.S. Pat. No. 3,628,524, inter alia, to Jamshidi, and U.S. Pat. No. 7,278,972 to Lamoureux, et al.). The needle is twisted down through the cortex of the bone into the marrow space. Once the marrow cavity is accessed, the trocar is removed and a syringe is attached to the opening where the trocar resides. A liquid sample can be withdrawn from the marrow space using the syringe attached to the needle. Alternatively, a core sample of marrow can be obtained. The hollow center of the cannula needle is specially shaped with a first proximal diameter, tapering to a distal end of a second diameter. The needle is tapered in the last 2 to 3 centimeters of the distal end to a smaller sharpened opening with a cutting edge. This reduced second diameter of the large bore needle assists in capturing and holding a core sample instead of a liquid sample.

To obtain a core sample using this Jamshidi (R) method, the bone cortex is penetrated in the same manner as for a liquid sample, but once the trocar is removed, the hollow cannula is driven farther manually, into the marrow space, to obtain a solid core of marrow. A core sample of a certain length is obtained by inserting a rod into the cannula, and driving the cannula into the marrow until the proximal end of the rod rises to the desired length above the proximal end of the cannula. To preserve the integrity of the core sample, the physician rocks the needle from side to side to break the distal end of the sample free from the rest of the matrix of marrow. The cannula is then removed from the patient and the marrow sample is removed by pushing the rod all the way through the cannula, discharging the sample into a sample bottle.

This apparatus and method are widely used because the apparatus is single-use disposable and reasonably priced. The main drawback of this apparatus and method is that it requires significant manual axial pressure and rotation to drive the needle through the bone cortex, all the while attempting to sense the interface between the cortex and the marrow and avoid either penetrating the marrow completely or mechanically damaging the marrow before a sample can be obtained. Even the most skilled practitioners often find it necessary to reinsert the instrument, causing another wound and taking more time.

The manual procedure has been improved more or less, cost notwithstanding, by automated devices. A number of prior art devices automate obtaining biopsies, but most of them are suitable for soft tissue use only. (See, e.g., U.S. Pat. No. 7,189,207 to Viola, comprising a trocar driver, a knife driver and firing module.) U.S. Pat. No. 4,919,146 to Rhinehart incorporates an electric drill and a syringe into a hand-held device, but the patent specification does not mention bone or marrow biopsy nor does the device appear to be suitable for those procedures. In any case, it appears that the drill bit of Rhinehart will not produce a core sample with sound architecture. One prior art device intended to solve the problem of manual control and get a good intra osseous sample in one operation is U.S. Pat. No. 6,022,324 to Skinner, comprising a sampling needle driven by a gun which applies axial bone-penetrating force of up to 200 pounds. This force is supplied by an electric motor or gas cylinder. It incorporates a syringe to withdraw a sample after actuation of the firing mechanism. A problem here is that, while it reduces the time required to get a sample, it would seem not to provide sufficient sample quality and reproducibility because of the wide patient-to-patient variation in soft tissue depth and thicknesses of bone cortex and marrow, and the likely trauma caused by the impact of the syringe on the tissues. A later patent, U.S. Pat. No. 6,626,848 to Neuenfeldt, moves the sampling needle in a reciprocal rotating motion about its axis as it is guided into the bone and thence into the marrow. The sampling is performed in a manner similar to the aforementioned Jamshidi method after the bone cortex is penetrated. The unsolved problem here is that no provision is made for withdrawal of both liquid and solid samples in one operation and the use of relatively-inexpensive tissue-contacting parts for disposal.

What is needed is a power-driven device that not only accomplishes the above-mentioned goals of improved sampling success and reduced time requirement, but also improves, rather than diminishes, the physician's tactile sense of cannula placement. It is also highly desirable to provide these qualities in a device that has single-use disposable tissue and liquid contact parts, the parts being of simple construction and reasonable price, operable by a mechanism that does not require large capital investment.

BRIEF DESCRIPTION OF INVENTION

This invention comprises an ergonomic handle containing a driver, with a detachable and disposable sterile single use cannula/trocar and disposable vacuum containers. The drill cannula has a crown tip and smooth external and internal surfaces to allow accurate cutting with minimal tissue trauma and maximum sample integrity. The driver has a control switch enabling either variable speed forward, neutral, or variable speed reverse axial rotation of the drill cannula, the driver motor being either electric, compressed air, or vacuum operated. The handle optionally further comprises a vacuum trigger to supplement withdrawal of a suitable liquid sample while the cannula is still inserted into the patient. The device and method for use improve the ability of a physician to locate accurately the target tissue in a patient, increase the probability that one or more suitable samples will be recovered from the patient at a single attempt, and decrease attendant tissue trauma and patient discomfort.

DETAILED DESCRIPTION OF INVENTION

Figure 1:
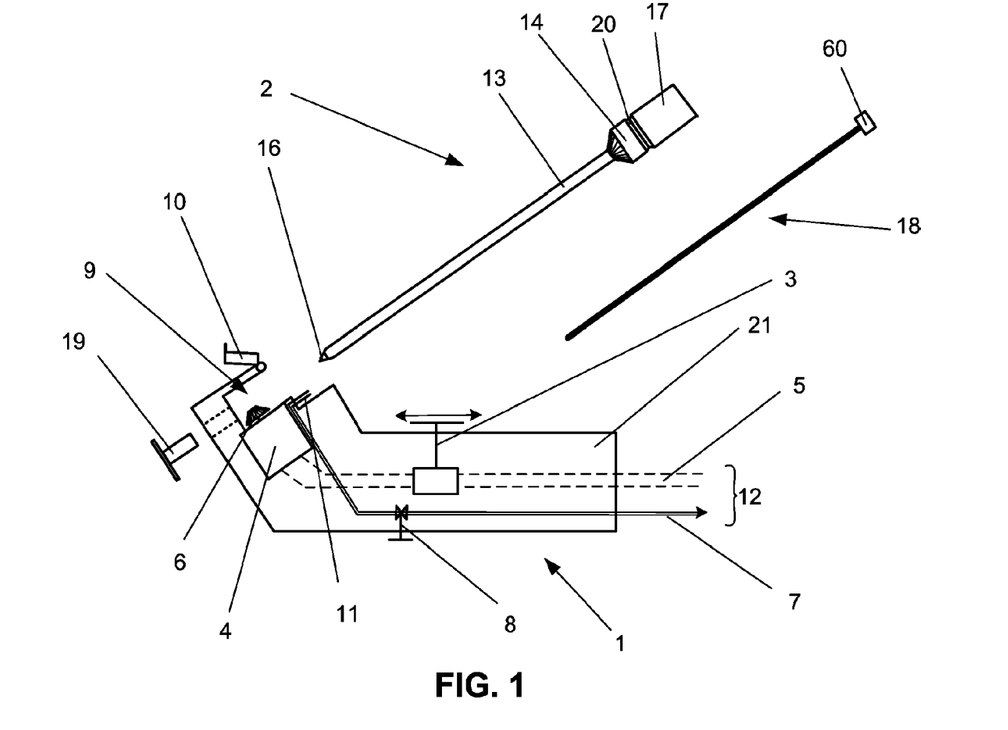
FIG. 1 is a schematic diagram of the invention being prepared for use.

Referring now to the drawings, in which like elements in each drawing are represented by like reference numerals, FIG. 1 is a schematic diagram of the invention being prepared for use. It consists of a permanent reusable driver portion 1 and principal sterile disposable parts including drill 2, spacing stylet 18 and bushing 19. Spacing stylet 18 has a button 60 to allow aseptic handling of the rest of the stylet. Driver portion 1 includes a handle 21, a control switch assembly 3, a motor 4, motor power input 5, a driven bevel gear 6, an optional vacuum source 7, an optional vacuum switch assembly 8, a drill chamber 9, a latch 10, and an optional vacuum needle 11. The motor 4 may be electric, compressed air, or vacuum operated. If operated by electricity, it can be battery powered or utilize AC power through power input 5. It is controlled by switch assembly 3, which may toggle forward, neutral, or rearward to drive motor 4, and, in turn, rotate bevel gear 6, clockwise, neutral, or counterclockwise. Vacuum may be applied to a sample container (see below) by pressing the trigger on optional vacuum switch assembly 8 to allow optional vacuum source 7 to pull a vacuum at optional vacuum needle 11. Note that vacuum source 7 and power input 5 may be combined into a utility cable 12. Drill 2 consists of cannula 13, cannula gear 14, and a trocar 15 (see FIG. 2 below, only trocar tip 16 and trocar cap 17 are visible in this view). Cannula 13 is hollow along its entire length and trocar 15 is slidably removable within it. The cannula optionally may be tapered as in Jamshidi with conforming trocar shape to help retain a solid marrow sample if desired.

Trocar cap 17 is removably attached to the top of cannula gear 14 by frangible connector 20. To prepare the device initially for use, disposable bushing 19 is inserted into a receiving hole 22 in the bottom of drill chamber 9, and drill 2 is inserted downwardly through bushing 19 until cannula gear 14 meshes with bevel gear 6, and latch 10 can secure drill 2 in place. The bushing isolates all of the non-disposable portions of the invention from contact with the patient.

Figures 2, 2A:
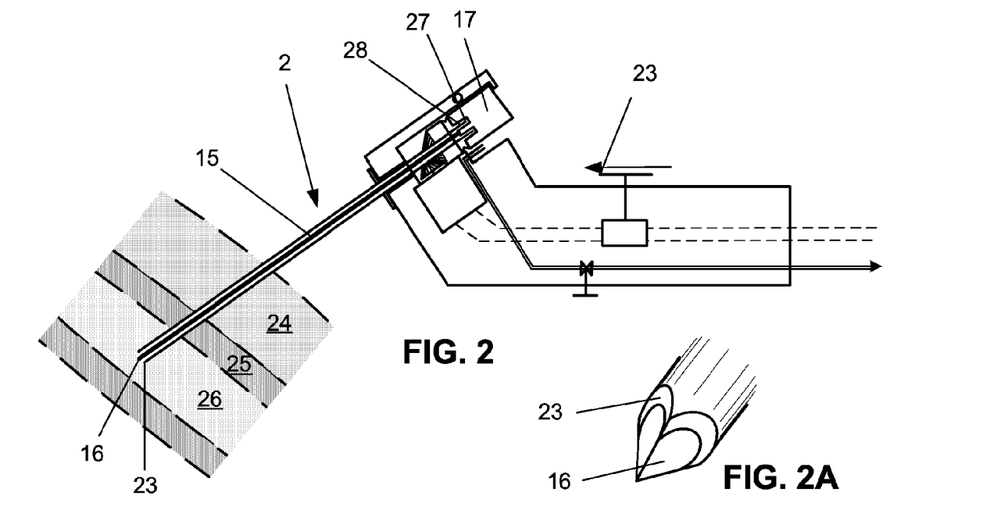
FIG. 2 is a schematic diagram of the invention being advanced into the tissue of a patient.

FIG. 2 is a schematic diagram of the invention after having been advanced into the tissue of a patient by pressing thumb switch 23 forward to drive drill 2 clockwise. Drill 2 is cut away lengthwise in this view so that trocar 15 can be seen within cannula 13. Also visible here is that trocar cap 17 is fixed to the upper end of trocar 15, and it has an annular recess 27 that covers a syringe tip 28 at the top of cannula 13. Cannula 13 has, at its other end, a crown tip 23, and trocar 15 has a matching trocar tip 16 which together enable cutting through soft tissue and bone with minimal tissue damage. Inset FIG. 2A shows magnified detail of crown tip 23 and trocar tip 16. In FIG. 2, drill 2 has been advanced through an outer tissue layer 24 and bone cortex 25 of a patient (shown in dashed lines as environmental structure). When bone is reached, the physician senses it by increased resistance to forward motion, just as would be the case with the Jamshidi (R) set, but the cannula keeps moving forward as long as the physician continues to exert pressure on the handle an continues to hold the switch in direction A. Whereas a physician must apply considerable repetitive manual pushing and twisting to advance the Jamshidi (R) set, accompanied by a certain amount of pressure discomfort to the patient, reaching the bone marrow with the instant invention is achieved smoothly with very little impact. Reaching bone with the instant invention is sensed by increased torque on the handle and decreased drill speed. The physician can now carefully control the rate of advancement of the drill until the cortex is penetrated. At that point, the physician can feel the decreased resistance to forward motion and increased drill speed. The physician's sense of touch is important here in preventing over extensive drilling, and the shape of handle 21 (see FIGS. 14-16) augments that by causing the reactive force of the handle to be applied against the fingers instead of the palm of the hand. The physician is now free to select any drill speed or no speed to advance the drill into the marrow cavity 26.

Figure 3:
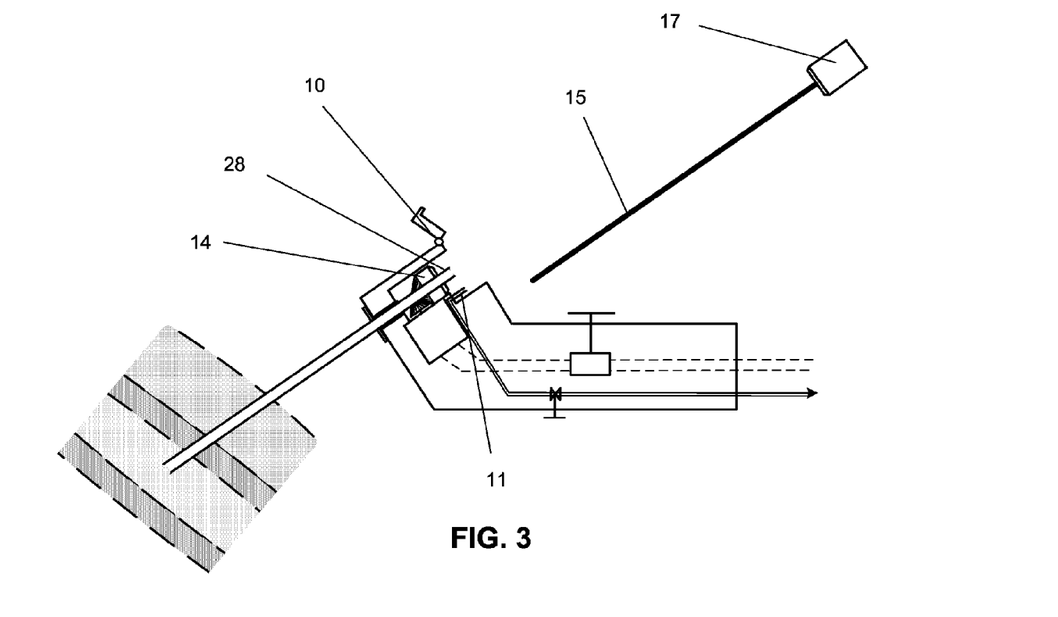
FIG. 3 is a schematic diagram of the invention with trocar removed prior to sampling.

FIG. 3 is a schematic diagram of the invention with trocar 15 removed prior to withdrawal of a liquid sample. Latch 10 is now opened allowing trocar cap 17 to be broken free of cannula gear 14. Note that cannula syringe tip 28 and optional vacuum needle 11 are now exposed.

Figure 4:
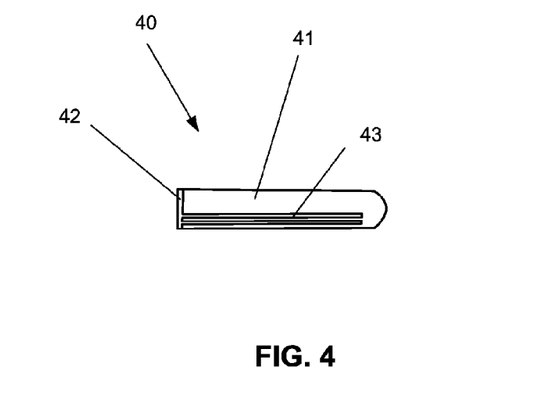
FIG. 4 is a schematic diagram of the evacuated sample container of the invention.

FIG. 4 is a schematic diagram of the evacuated sample container 40. It consists of an evacuated sterile test tube 41 having a frangible seal, such as a septum 42, at one end. The septum may further comprise an optional vacuum inlet tube 43 molded in unitary fashion with septum 42.

Figure 5:
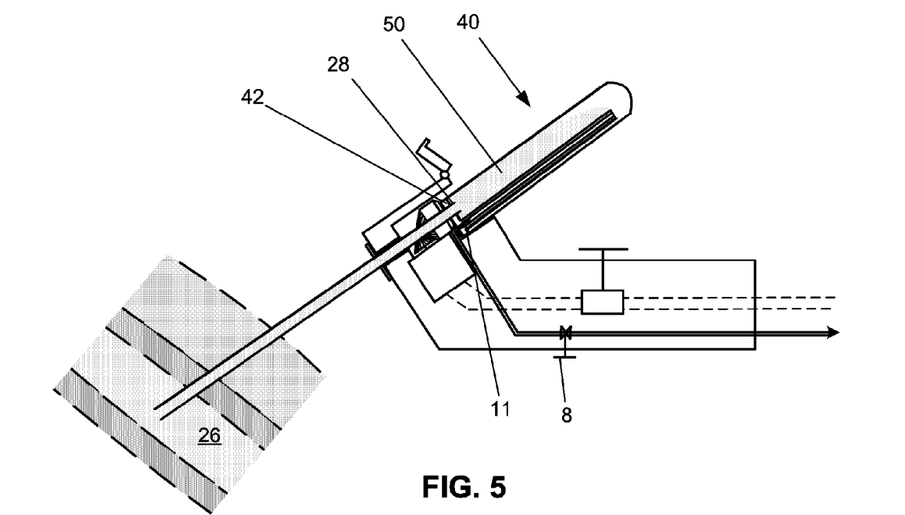
FIG. 5 is a schematic diagram of the evacuated container being used to collect a liquid marrow sample.

FIG. 5 is a schematic diagram of the evacuated container 40 being used to collect a liquid marrow sample. Sample tube 40 has been pressed down over syringe tip 28 and optional vacuum needle 11 which both penetrate septum 42. The vacuum in the tube has sucked the liquid 50 from the marrow cavity 26 into tube 40. If additional vacuum assist is necessary to pull liquid into the tube, vacuum switch assembly 8 may be actuated by the user.

Figure 6:
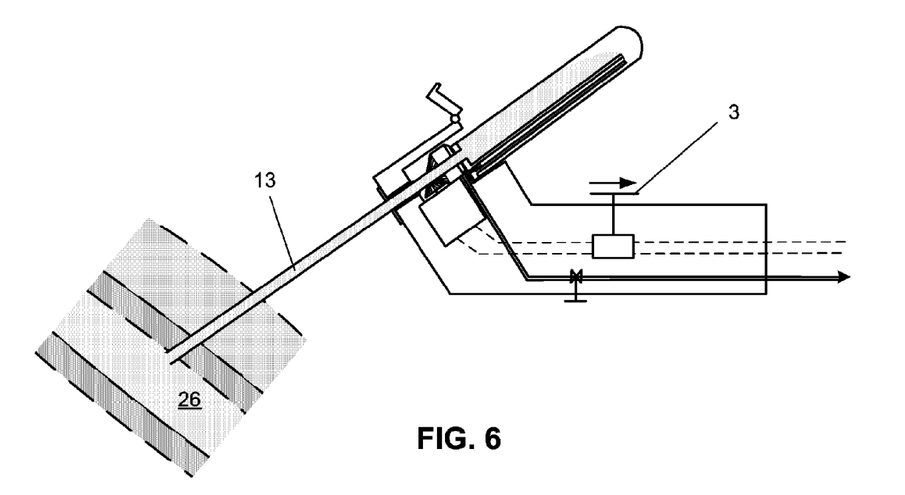
FIG. 6 is a schematic diagram of the invention being partially withdrawn for repositioning to collect a solid marrow sample.

FIG. 6 is a schematic diagram of the invention being partially withdrawn from the marrow cavity 26 for repositioning to collect a solid marrow core sample. Repositioning the cannula by partial withdrawal and re-insertion into an undisturbed portion of the marrow cavity is desirable because it improves the likelihood that the solid sample will accurately represent the patient's marrow structure, and it reduces the chance that continued drilling through the marrow will cut into the bone on the other side. Control switch assembly 3 is pulled into reverse to drive cannula 13 counterclockwise if necessary.

Figure 7:
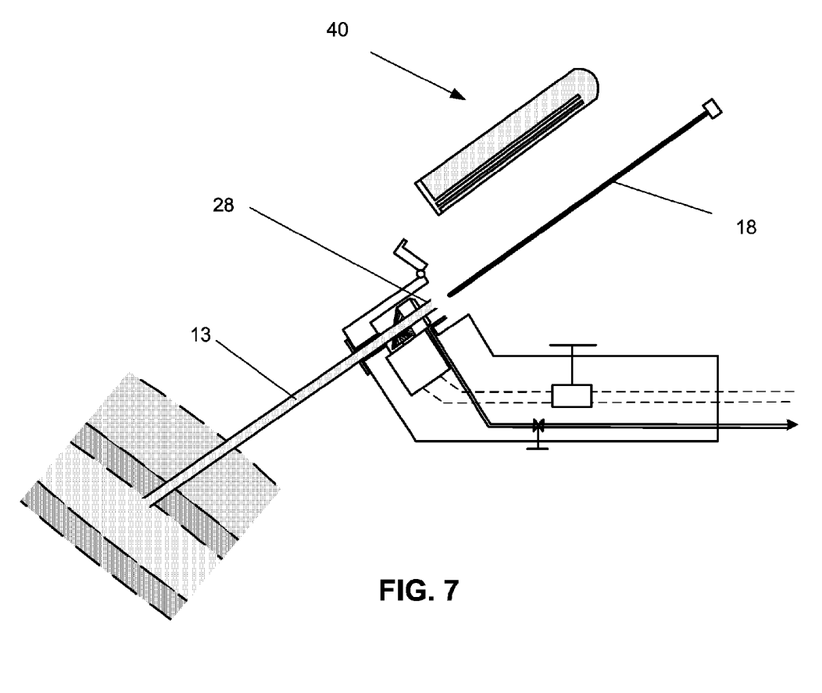
FIG. 7 is a schematic diagram showing the evacuated sample container being removed and the spacing stylet being inserted in preparation for obtaining a solid marrow sample.

FIG. 7 is a schematic diagram showing the evacuated sample container 40 removed and the sterile spacing stylet 18 being inserted into syringe tip 28 of cannula 13 in preparation for obtaining a solid marrow core sample.

Figure 8:
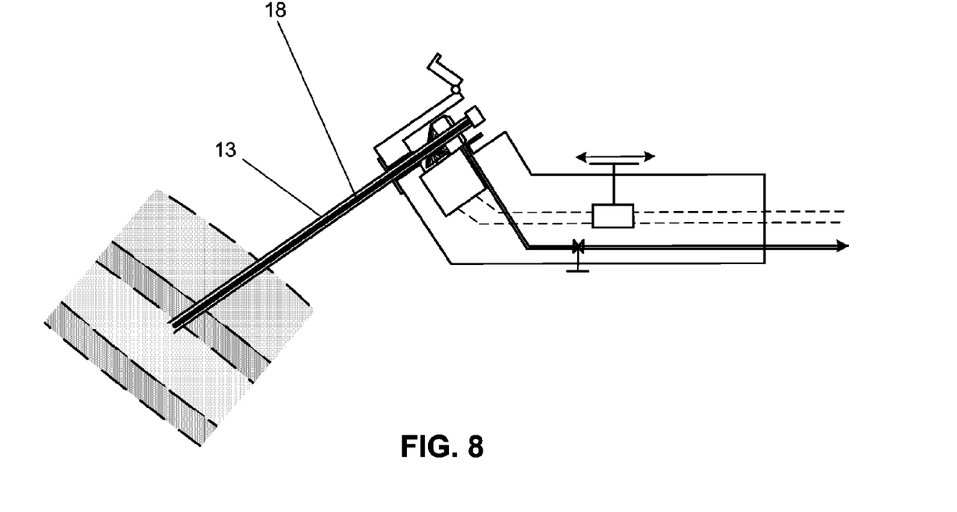
FIG. 8 is a schematic diagram showing the invention with the spacing stylet fully inserted into the cannula.

FIG. 8 is a schematic diagram showing the invention with the spacing stylet 18 fully inserted into the cannula 13, initially pushing liquid out of the cannula 13 and back into the marrow cavity, thereby making room for a solid marrow sample. The spacing stylet 18 can be made from any material that maintains its approximate length for spacing purposes. It can be made from liquid-wicking material such as a hydrophilic open-cell foam, which would allow it to soak up liquid as it is inserted into cannula 13, thereby preventing liquid from emerging from the cannula 13 into the surrounding area.

Figure 9:
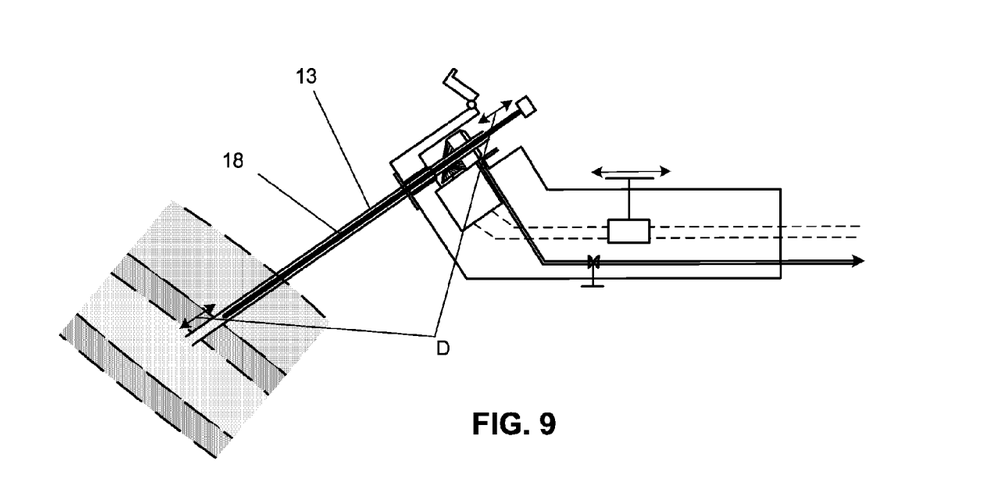
FIG. 9 is a schematic diagram showing the spacing stylet partially withdrawn for solid sample collection.

FIG. 9 is a schematic diagram showing the spacing stylet 18 partially withdrawn from cannula 13 for solid sample collection. This is one method of collection allowing predetermination of the approximate length of the core. The distance D withdrawn is a matter of physician's judgment as to how long the sample core should be. If stylet 18 is made from liquid-wicking material, it is less likely to draw contamination down into the cannula 13 when stylet 18 is raised, and it allows liquid to rise up into the cannula 13 when cannula 13 encounters solid matter. Another method of measuring the core is to leave the stylet 18 fully in, and watch it rise to the desired core length when cannula 13 is drilled down into undisturbed solid marrow. Here again, liquid-wicking, but substantially rigid, stylus material will be pushed upward by solid matter but not by liquid.

Figure 10:
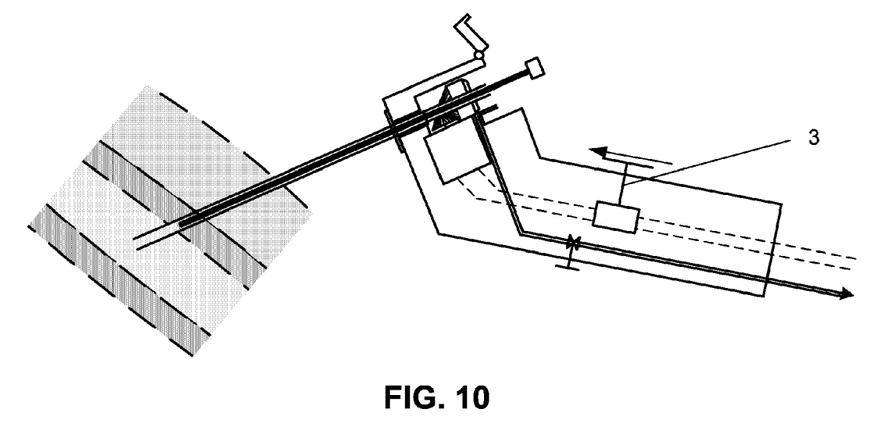
FIG. 10 is a schematic diagram showing the invention tilted and drilled into undisturbed marrow.

FIG. 10 is a schematic diagram showing the invention tilted downwardly (clockwise in this view) and drilled farther into undisturbed marrow by actuating control switch assembly 3 forward. A common syringe (not shown) may be applied to syringe tip 28 if necessary to assist in drawing solid matter into the cannula 13.

Figure 11:
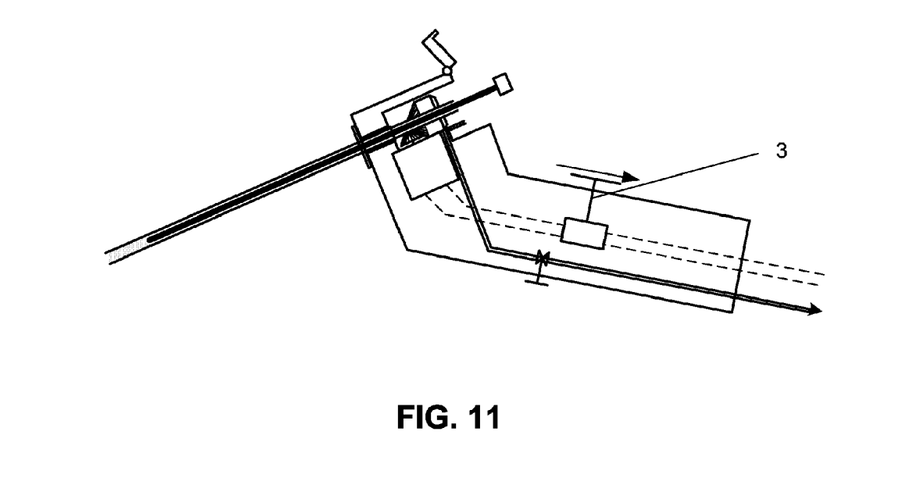
FIG. 11 is a schematic diagram showing the invention finally withdrawn from the patient.

FIG. 11 is a schematic diagram showing the invention finally withdrawn from the patient by actuating control switch assembly 3 in reverse.

Figure 12:
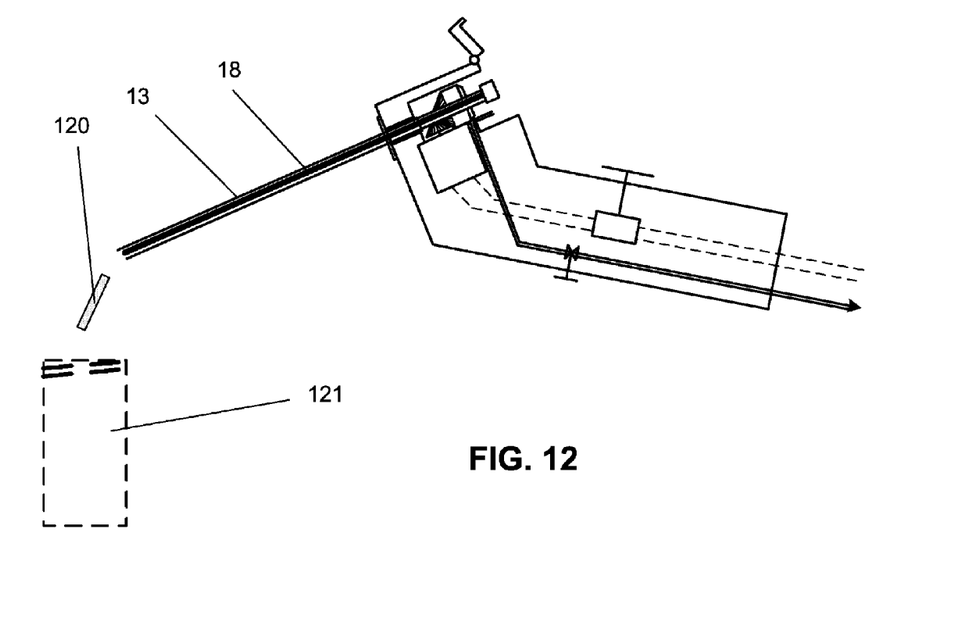
FIG. 12 is a schematic diagram showing the spacing stylet used to push the solid sample from the cannula.

FIG. 12 is a schematic diagram showing the spacing stylet 18 used to push the solid sample 120 from the cannula 13 into a sample bottle 121 (shown in dashed lines as environmental structure).

Figure 13:
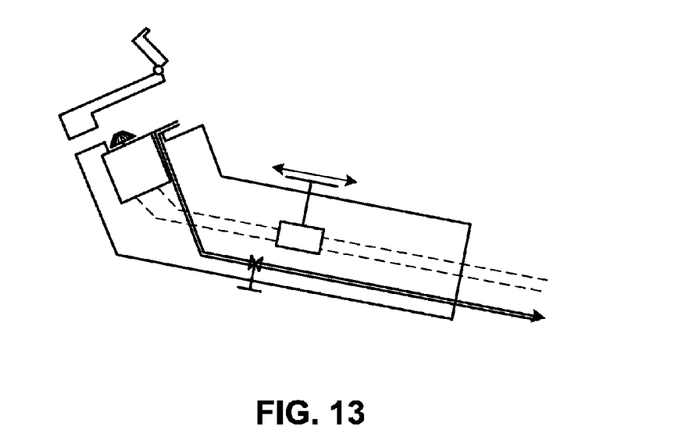
FIG. 13 is a schematic diagram of the invention with all disposable parts discarded.

FIG. 13 is a schematic diagram of the invention with all disposable parts discarded.

Figure 14:
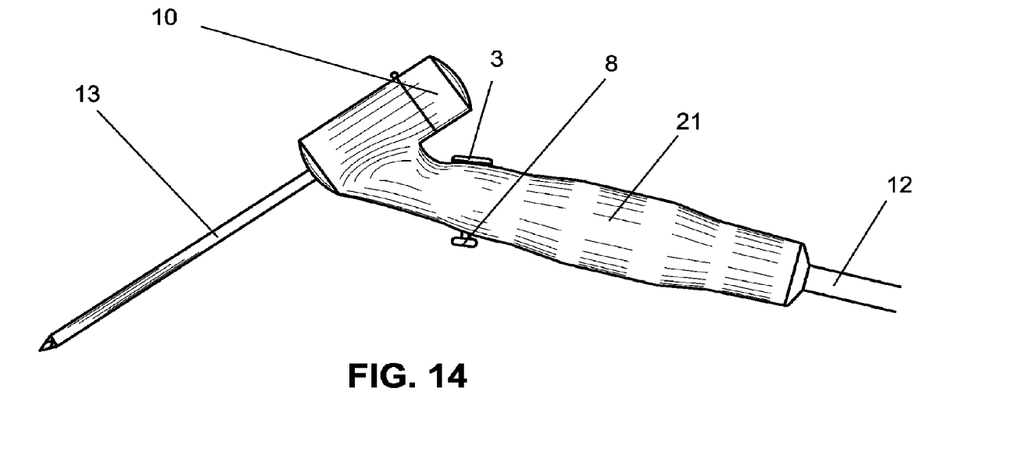
FIG. 14 is a side view of the preferred embodiment of the invention.

FIG. 14 is a side view of a preferred, ergonomically-shaped embodiment of the invention, containing the elements shown in the preceding schematic diagrams. It is operable with one hand, having a smooth case to create maximum contact with the inner surface of the hand, in the manner of a dental drill. Unlike a dental drill, however, the axis of the handle is nearly in line with the axis of the drill, preferably off collinear by no more than about 30 degrees, for optimum tactile responsiveness. This is because all of the thrust of this operation is forward, rather than upwards or downwards. Handle 21 has control switch assembly 3 arranged upon it so that it can be actuated forward, neutral or reverse by a thumb, and it has vacuum switch assembly 8 placed so that it can be actuated upwardly by a forefinger. Note also the embodiment of visible features latch 10, utility cable 12, and cannula 13. Other shapes of driver portion 1, handle 21 and latch 10 not depicted here, but which are sized and shaped so as to accommodate all of the other elements depicted in the foregoing schematics, are included within the scope of this invention without limitation.

Figure 15:
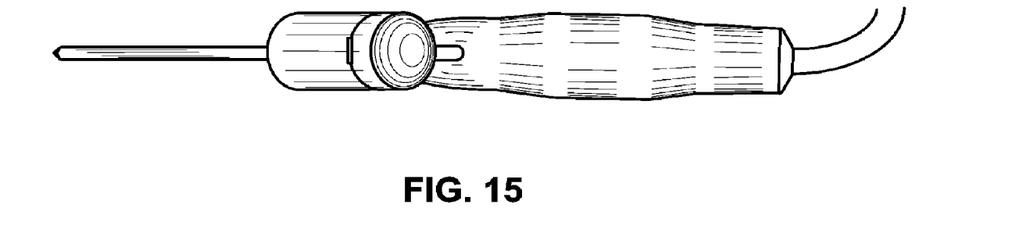
FIG. 15 is a top view of the preferred embodiment of the invention.

FIG. 15 is a top view of the preferred embodiment of the invention.

Figure 16:
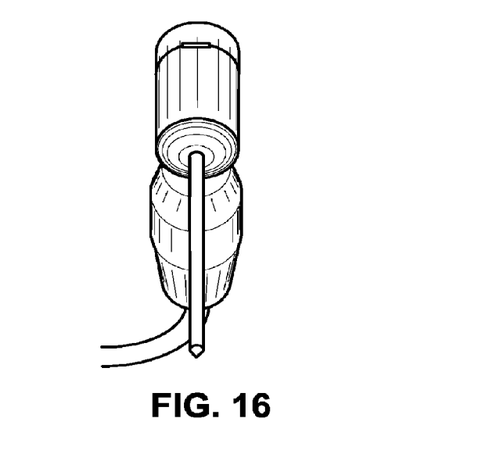
FIG. 16 is a front view of the preferred embodiment of the invention.

FIG. 16 is a front view of the preferred embodiment of the invention.

The invention claimed is:

1. A bone tissue extracting device, comprising:
 a driver portion comprising
  a handle;
  a motor;
  a user-operated motor actuator for controlling the motor;
  a driven gear;
 a drill portion;
  the drill portion adapted to fit into the driver portion, comprising a hollow, elongate cannula having a proximal end and a distal end, the cannula comprising
   a first means for piercing a frangible seal at the proximal end;
   a cannula gear engaged near the proximal end to co-rotate coaxially with the cannula, the cannula gear located on a distally facing surface of the proximal end,
   the cannula gear adapted to mesh with the driven gear;
   and an elongate trocar having an upper end and a lower end and shaped to fit slidably and coaxially into, and removably from, the cannula;
   the upper end of the trocar comprising a cap;
   the cap having a center and a periphery;
   the center being attached to the upper end of the trocar;
   the cap covering the first means for piercing a frangible seal at the proximal end of the cannula;
    the periphery being directly and removably connected to the cannula gear
   so that when the removable connection is actuated, the trocar can be removed from the cannula;
  the drill portion being rotatable by the motor through operation of the user-operated motor actuator, thereby allowing a user of the device to advance and withdraw the cannula into and out of the bone tissue of a patient.

2. The device of claim 1, further comprising:
 a receptacle sealed by a frangible seal;
 said first means for piercing a frangible seal being exposed by actuating said removable connection to provide a first fluid passage from said cannula into the receptacle sealed by a frangible seal.

3. The device of claim 2, further comprising:
 means for applying a vacuum to said receptacle sealed by a frangible seal.

4. The device of claim 3, in which:
 said means for applying a vacuum to said receptacle sealed by a frangible seal comprises
  means for creating a vacuum and a second means for piercing a frangible seal located inside said driver portion; and
  a user-operated vacuum actuator on said handle to control the amount of vacuum applied to said receptacle sealed by a frangible seal.

5. The device of claim 1, in which:
 said means for removable connection is taken from the list consisting of:
 (a) a frangible connection between said periphery and said cannula gear, and
 (b) threads on said periphery mating with threads on said cannula gear.

6. The device of claim 1, in which:
 said drill portion further comprises
  an elongate stylus shaped to fit slidably into said cannula.

7. The device of claim 6, in which:
said elongate stylus comprises liquid-wicking material.

8. A method for using the device of claim 6, comprising the steps of:
(a) fitting said drill portion into said driver portion;
(b) advancing said drill portion into the patient by pressing said handle toward the patient and actuating said user-operated motor actuator to rotate said drill portion as necessary until the desired location for drawing a sample is reached;
(c) actuating said removable connection and removing said trocar from said cannula;
(d) applying said receptacle sealed by a frangible seal to at least said first means for piercing a frangible seal;
(e) collecting a bone marrow sample in said receptacle sealed by a frangible seal by actuating said vacuum actuator and said user-operated motor actuator as necessary;
(f) withdrawing said drill portion from the patient and removing said receptacle sealed by a frangible seal from said means for piercing a frangible seal.

9. The method of claim 8, adding after step (e) and ahead of step (f) the steps of:
(e)(1) removing said receptacle sealed by a frangible seal from said means for piercing a frangible seal without removing said drill portion from the patient;
(e)(2) inserting said stylus into said cannula to a position desired by the user;
(e)(3) actuating said user-operated motor actuator as necessary to position said cannula for drawing a second sample;
(e)(4) collecting a second sample by actuating said user-operated motor actuator as necessary to indicate collection of the second sample according to the position of said stylus desired by the user within said cannula.

10. A method for using the device of claim 6, comprising the steps of:
(a) fitting said drill portion into said driver portion;
(b) advancing said drill portion into the patient by pressing said handle toward the patient and actuating said user-operated motor actuator to rotate said drill portion as necessary until the desired location for drawing a sample is reached;
(c) actuating said removable connection and removing said trocar from said cannula;
(d) inserting said stylus into said cannula to a position desired by the user;
(e) actuating said user-operated motor actuator as necessary to position said cannula for drawing a sample;
(f) collecting the sample by actuating said user-operated motor actuator as desired by the user according to the position of said stylus desired by the user within said cannula;
(g) withdrawing said drill portion from the patient;
(h) removing the sample from said cannula.

11. A bone tissue extracting device, comprising:
a handle;
a motor;
an elongate, hollow cannula adapted to be attachable to, and driven in axial rotation by, the motor;
a cannula gear, adapted to be driven by the motor, engaged near the proximal end to co-rotate coaxially with the cannula, the cannula gear located on a distally facing surface of the proximal end;
the cannula having a proximal end and a distal end, the cannula comprising an elongate trocar having an upper end and a lower end and shaped to fit slidably and coaxially into, and removably from, the cannula;
the upper end of the trocar comprising a cap;
the cap having a center and a periphery;
the center being attached to the upper end of the trocar;
the cap covering the proximal end of the cannula;
the periphery being directly and removably connected to the cannula gear so that when the removable connection is actuated, the trocar can be removed from the cannula.

12. The device of claim 11, further comprising:
a receptacle sealed by a septum;
said proximal end of said cannula comprising a syringe tip to pierce the septum;
said handle comprising a vacuum needle parallel to the syringe tip to pierce the septum;
means for creating a vacuum located inside said handle; and
the means for creating a vacuum connected to the vacuum needle and controllable by a user.

13. The device of claim 11, further comprising:
a stylus adapted to fit slidably within said cannula.

14. The device of claim 13, in which:
said stylus is comprised of liquid-wicking material.

15. The device of claim 12, further comprising:
a stylus adapted to fit slidably within said cannula.

16. The device of claim 15, in which:
said stylus is comprised of liquid-wicking material.

17. A drill part for a bone tissue extractor, comprising:
a hollow, elongate cannula having a proximal end and a distal end, the cannula comprising
a means for removably engaging a motor drive shaft engaged near the proximal end to co-rotate coaxially with the cannula and located on a distally facing surface of the proximal end;
a means for piercing a frangible seal at the proximal end;
an elongate trocar having an upper end and a lower end and shaped to fit slidably and coaxially into, and removably from, the cannula;
the upper end of the trocar comprising a cap;
the cap having a center and a periphery;
the center being attached to the upper end of the trocar;
the cap covering the means for piercing a frangible seal at the proximal end of the cannula;
the periphery comprising means for directly and removably connecting the periphery to the means for removably engaging a motor drive shaft so that when the removable connection is actuated, the trocar can be removed from the cannula.

18. The device of claim 17, in which:
said means for removably connecting the periphery to the proximal end of the cannula is taken from the list consisting of:
(a) a frangible connection between said periphery and said proximal end of said cannula, and
(b) threads on said periphery mating with threads on said proximal end of said cannula.

* * * * *